United States Patent
Sokhi et al.

(10) Patent No.: US 11,440,912 B2
(45) Date of Patent: Sep. 13, 2022

(54) PROCESS FOR THE PREPARATION OF RIBOCICLIB AND ITS SALTS

(71) Applicant: FRESENIUS KABI ONCOLOGY LIMITED, New Delhi (IN)

(72) Inventors: Sarbjot Singh Sokhi, Haryana (IN); Govind Singh, Haryana (IN); Saswata Lahiri, Haryana (IN); Maneesh Kumar Pandey, Haryana (IN); Raj Narayan Tiwari, Haryana (IN); Sonu Shukla, Haryana (IN); Sachin Musmade, Haryana (IN); Heena Dua, Haryana (IN); Walter Cabri, Milan (IT)

(73) Assignee: FRESENIUS KABI ONCOLOGY LTD, New Delhi (IN)

( * ) Notice: Subject to any disclaimer, the term of this patent is extended or adjusted under 35 U.S.C. 154(b) by 0 days.

(21) Appl. No.: 16/758,773

(22) PCT Filed: Oct. 26, 2018

(86) PCT No.: PCT/IB2018/058376
§ 371 (c)(1),
(2) Date: Apr. 23, 2020

(87) PCT Pub. No.: WO2019/082143
PCT Pub. Date: May 2, 2019

(65) Prior Publication Data
US 2020/0277295 A1 Sep. 3, 2020

(30) Foreign Application Priority Data
Oct. 27, 2017 (IN) .............................. 201711038128

(51) Int. Cl.
C07D 487/04 (2006.01)
B01J 23/72 (2006.01)
C07D 401/04 (2006.01)

(52) U.S. Cl.
CPC ............ C07D 487/04 (2013.01); B01J 23/72 (2013.01); C07D 401/04 (2013.01); *C07B 2200/13* (2013.01)

(58) Field of Classification Search
CPC .................................................. C07D 487/04
USPC ........................................................ 544/280
See application file for complete search history.

(56) References Cited

U.S. PATENT DOCUMENTS

| 7,713,994 | B2 | 5/2010 | Tsou et al. |
| 9,969,719 | B2 | 5/2018 | Ding et al. |
| 9,994,579 | B2 | 6/2018 | Chen et al. |
| 10,308,654 | B2 | 6/2019 | Cheng et al. |
| 10,570,141 | B2 | 2/2020 | Wang et al. |
| 2017/0342075 | A1 | 11/2017 | Chen et al. |
| 2018/0072707 | A1 | 3/2018 | Ding et al. |
| 2018/0127419 | A1 | 5/2018 | Cheng et al. |
| 2018/0305363 | A1 | 10/2018 | Liu et al. |
| 2019/0300533 | A1 | 10/2019 | Wang et al. |
| 2020/0165239 | A1 | 5/2020 | Yin et al. |

FOREIGN PATENT DOCUMENTS

| CN | 105153149 A | 12/2015 |
| CN | 105622638 A | 6/2016 |
| CN | 106608879 A | 5/2017 |
| CN | 106905245 A | 6/2017 |
| CN | 105085533 B | 1/2018 |
| CN | 107936029 A | 4/2018 |
| CN | 105622638 B | 10/2018 |
| WO | WO 2005/011654 A2 | 2/2005 |
| WO | WO 2006/095159 A1 | 9/2006 |
| WO | WO 2007/075783 A2 | 7/2007 |
| WO | WO 2008/007123 A2 | 1/2008 |
| WO | WO 2008/032157 A2 | 3/2008 |
| WO | WO 2010/020675 A1 | 2/2010 |
| WO | WO 2011/130232 A1 | 10/2011 |
| WO | WO 2011/140488 A1 | 11/2011 |
| WO | WO 2012/064805 A1 | 5/2012 |

(Continued)

OTHER PUBLICATIONS

IP Australia, Examination Report No. 2 in Australian Patent Application No. 2018354972 (dated May 19, 2021).
Anonymous, "Process for preparation of Tert-Butyl 4-(6-(7-cyclopentyl-6-(dimethylcarbamoyl)-7H-pyrrolo[2,3-d]pyrimidin-2-ylamino)pyridin-3-yl)piperazine-1-carboxylate," IP.com Prior Art Database Technical Disclosure (Mar. 18, 2018) 5 pgs.

(Continued)

*Primary Examiner* — Charanjit Aulakh
(74) *Attorney, Agent, or Firm* — Leydig, Volt & Mayer, Ltd.

(57) ABSTRACT

The invention relates to a process for the preparation of ribociclib of formula V or its salts. The invention provides novel crystalline forms of ribociclib succinate and ribociclib trifluoroacetate. The present invention also relates to pharmaceutical compositions comprising a crystalline form of ribociclib succinate and at least a pharmaceutically acceptable carrier. It further relates to the use of such compositions in the treatment of cancer.

(V)

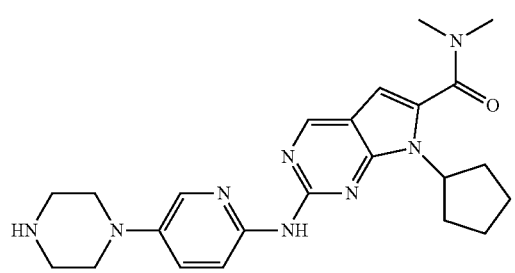

11 Claims, 3 Drawing Sheets

(56) References Cited

FOREIGN PATENT DOCUMENTS

| | | |
|---|---|---|
| WO | WO 2013/067274 A1 | 5/2013 |
| WO | WO 2013/090497 A1 | 6/2013 |
| WO | WO 2014/128588 A1 | 8/2014 |
| WO | WO 2014/195274 A1 | 12/2014 |
| WO | WO 2015/131080 A1 | 9/2015 |
| WO | WO 2016/030439 A1 | 3/2016 |
| WO | WO 2016/091221 A1 | 6/2016 |
| WO | WO 2016/141881 A1 | 9/2016 |
| WO | WO 2016/165657 A1 | 10/2016 |
| WO | WO 2016/194831 A1 | 12/2016 |
| WO | WO 2017/045648 A1 | 3/2017 |
| WO | WO 2017/092635 A1 | 6/2017 |
| WO | 2017/162215 A1 | 9/2017 |

OTHER PUBLICATIONS

Greene et al., "Protective Groups in Organic Synthesis," 3rd Ed., pp. 17-245, J. Wiley & Sons (1999).
European Patent Office, International Search Report in International Application No. PCT/IB2018/058376 (dated Apr. 4, 2019).
European Patent Office, Written Opinion in International Application No. PCT/IB2018/058376 (dated Apr. 4, 2019).
International Bureau of WIPO, International Prelimnary Report on Patentability in International Application No. PCT/IB2018/058376 (dated Apr. 28, 2020).

PROCESS FOR THE PREPARATION OF RIBOCICLIB AND ITS SALTS

CROSS REFERENCE TO RELATED PATENT APPLICATION(S)

This patent application is the U.S. national stage of International Patent Application No. PCT/IB2018/058376, filed on Oct. 26, 2018, which claims the benefits of Indian Patent Application No. 201711038128, filed on Oct. 27, 2017, the disclosures of which are incorporated by reference herein in their entireties for all purposes.

FIELD OF THE INVENTION

The present invention relates to an improved process for the preparation of a compound of formula I,

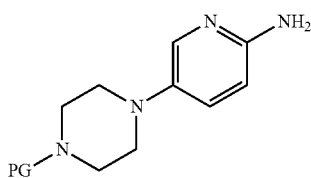

Formula I wherein, PG is an amine protecting group;
used in the synthesis of ribociclib or its salts.

The present invention also relates to an improved process for the conversion of the compound of formula I to a compound of formula III,

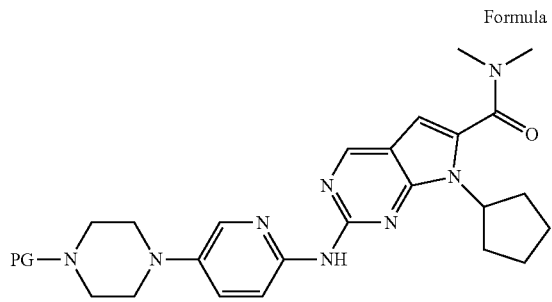

Formula III wherein PG is an amine protecting group.

The present invention further relates to an improved process for the synthesis of ribociclib or its salts, more particularly the succinate salt and trifluoroacetate salt of ribociclib is prepared.

The present invention further provides a green chemistry process for the preparation of a compound of the formula A,

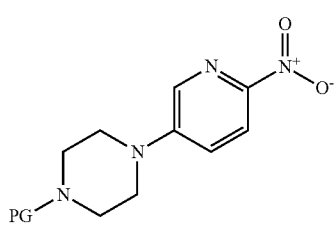

Formula A wherein PG is an amine protecting group;
used in the synthesis of ribociclib or its salts.

In another aspect, the present invention provides novel crystalline forms of ribociclib succinate and ribociclib trifluoroacetate. The present invention further provides processes for the preparation of such crystalline forms of ribociclib succinate and ribociclib trifluoroacetate.

The present invention also relates to pharmaceutical compositions comprising a crystalline form of ribociclib succinate and at least a pharmaceutically acceptable carrier. It further relates to the use of such compositions in the treatment of a patient in need thereof.

BACKGROUND OF THE INVENTION

Ribociclib, 7-cyclopentyl-N,N-dimethyl-2-((5-(piperazin-1-yl)pyridin-2-yl)amino)-7H-pyrrolo[2,3-d]pyrimidine-6-carboxamide, is represented by formula V,

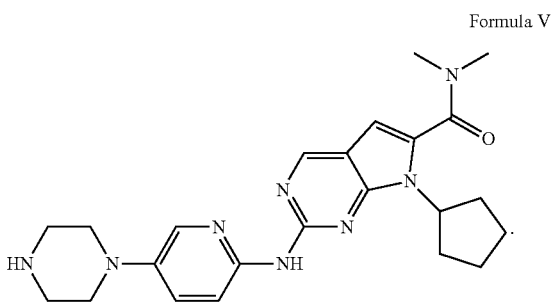 [SMILES: CN(C)C(=O)c1cc2cnc(Nc3ccc(N4CCNCC4)cn3)nc2n1C1CCCC1]

Formula V

Ribociclib is approved as its succinate salt, which is the active ingredient of the drug KISQALI™. The succinate salt of ribociclib is represented by formula VI,

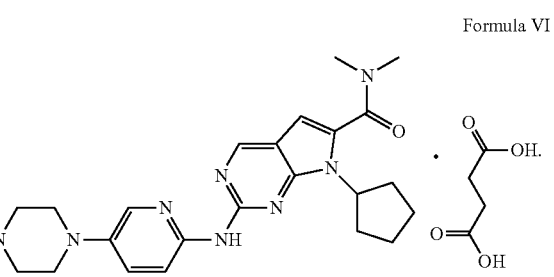

Formula VI

KISQALI™ is indicated in combination with an aromatase inhibitor as initial endocrine-based therapy for the treatment of postmenopausal women with hormone receptor (HR)-positive, human epidermal growth factor receptor 2 (HER2)-negative advanced or metastatic breast cancer.

Ribociclib, as represented by formula V is disclosed in WO 2010/20675. Example-74 of WO 2010/20675 describes that reaction of 2-chloro-7-cyclopentyl-7H-pyrrolo[2,3-d]pyrimidine-6-carboxylic acid dimethylamide with 5-piperazin-1-yl-pyridin-2-ylamine produces ribociclib via following the Buchwald Method B and then following general procedure A as described therein.

The Buchwald Method B described in WO 2010/20675 involves the use of reagents such as Pd$_2$(dba)$_3$, (2,2'-bis (diphenylphosphino)-1,1'-binaphthyl) (BINAP) and sodium-tert-butoxide. Subsequently, the obtained compound is purified by silica gel chromatography followed by deprotection using General Procedure A.

The reactants involved in Buchwald Method B do not contain a protecting group at any position, but the subsequent step, i.e. General Procedure A, demands for deprotection of the product obtained from Buchwald Method B. The yield and purity of the final compound are not mentioned.

3-yl)-piperazine-1-carboxylic acid tert-butyl ester (Formula Aa) in the presence of zinc dust and NH$_4$Cl.

US patent application Ser. No. 11/728,897 (U.S. Pat. No. 7,713,994 B2) discloses a process for the preparation of compound of formula Ia by reduction of 4-(6-nitro-pyridin-3-yl)-piperazine-1-carboxylic acid tert-butyl ester (Formula Aa) in the presence of iron and acetic acid.

The compound of the formula Aa is generally prepared by reacting 5-chloro-2-nitropyridine with N-protected piperazine or free base piperazine in the presence of a solvent as represented below:

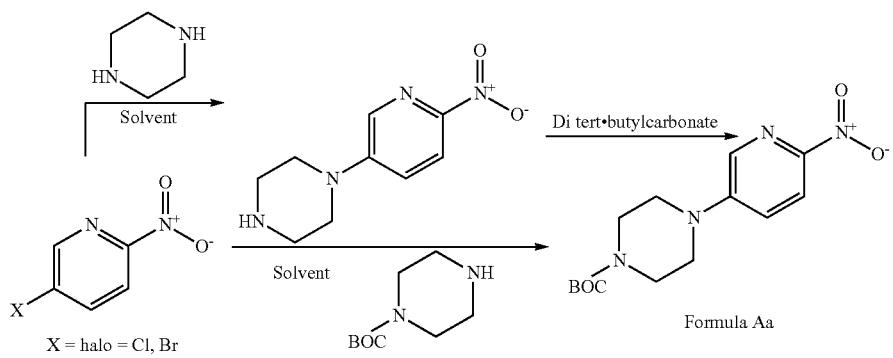

Scheme-1a

WO 2010/20675 also provides a process for the preparation of a compound of formula Ia as represented in scheme-1:

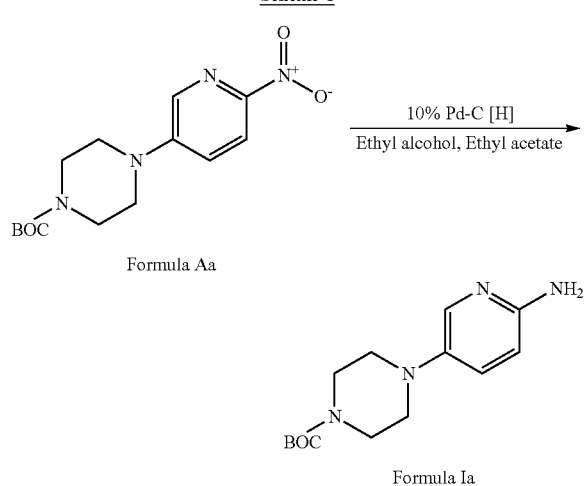

Scheme-1

There are other patent applications, such as CN 20141597511 (CN 105622638B) and US patent application Ser. No. 11/728,897 (U.S. Pat. No. 7,713,994 B2), which disclose the synthesis of compound of formula Ia.

Chinese application no. CN 20141597511 (CN 105622638B) discloses a process for the preparation of compound of formula Ia by reduction of 4-(6-nitro-pyridin- WO2012064805 discloses a process for the preparation of the compound of formula Aa by reacting 5-chloro-2-nitropyridine with piperazine in the presence of n-butanol. Subsequently, the obtained product is treated with di-tert-butyl dicarbonate to obtain the compound of formula Aa.

WO2014128588, WO2011140488, WO2016030439, WO13067274A1, WO16165657A1 and CN 105153149 discloses a process for the preparation of the compound of formula Aa, where 5-bromo-2-nitropyridine is reacted with BOC protected piperazine in the presence of DMSO.

WO13090497A1 discloses a process for the preparation of the compound of formula Aa by reacting 5-bromo-2-nitropyridine and N-boc piperazine in the presence of N-methylpyrrolidine.

In WO2017045648, the compound of formula Aa is prepared using microwave and DMSO as a solvent.

Similarly, WO2011130232, WO2010020675, WO17092635, CN106608879, WO08007123, WO2016141881, WO2014195274, WO2008032157, WO2015131080, WO2016194831, WO05011654, WO07075783, CN105622638, WO06095159 etc. provides the process for the preparation of compound of formula Aa using solvents such as acetonitrile, DMSO etc. which is less preferred for a process scale at least because of the inherent safety risks.

WO 2012/064805 describes a process for the preparation of ribociclib succinate which involves the reaction of the compound of formula Ia with the compound of formula II to obtain a compound of formula IIIa, as shown in scheme-2:

Scheme-2

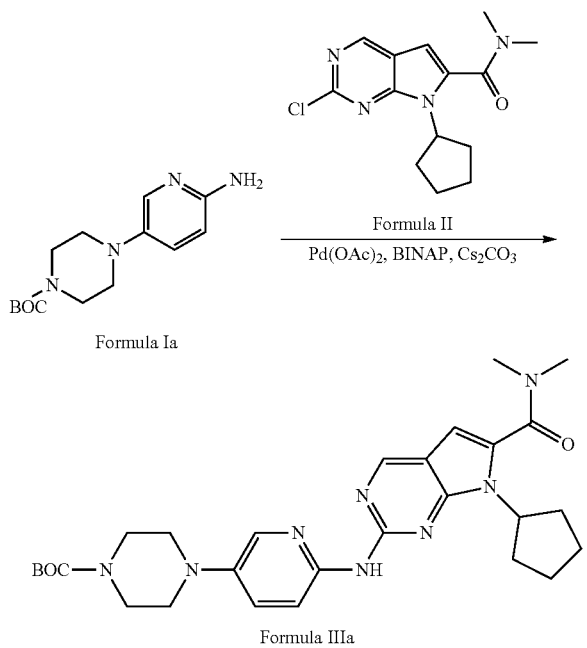

wherein BINAP represents (2,2'-bis(diphenylphosphino)-1,1'-binaphthyl), Cs$_2$O$_3$ is Cesium Carbonate.

The process described in WO 2012/064805 requires the use of expensive reagents such as BINAP and palladium catalyst etc. It further requires chromatographic purification of the obtained compound before its utilization in the next step. Reaction yield is ca. 55%. Purity is not specified.

Chinese application no. 20181018318.0 (published as CN 107936029A) describes the preparation of the compound of formula II by reaction of 2-chloro-7-cyclopentyl-6-methyl-7H-pyrrole[2,3-d] pyrimidine with aq. dimethylamine and N-chlorosuccinimide in 1,4-dioxane in presence of copper acetate as catalyst and t-butanol peroxide as an oxidizing agent and tetrabutylammonium iodide as an additive at 75° C. The compound of formula II is isolated and reacted with the compound of formula Ia in presence of potassium carbonate and dichloromethane to obtain compound of formula IIIa.

In the next step, the compound of formula IIIa is converted to ribociclib by deprotection using hydrochloric acid. The ribociclib (Formula V) is further converted to ribociclib succinate (Formula VI) by reaction with succinic acid in 2-propanol.

From the forgoing, it is apparent that the reported methods for the preparation of ribociclib or its salts require stringent operational conditions which are not only tedious but also result in significant yield loss. These processes require the use of expensive reagents and palladium catalysts.

Moreover, long work-up procedures and use of hazardous solvents at several stages and/or chromatographic purification make the process less attractive for commercial scale.

Thus, there remains a need to formulate an efficient, simple and industrially viable synthetic process which can overcome the drawbacks of the prior art and which provides ribociclib, its intermediates or salts thereof, substantially free of impurities.

WO 2012/064805 also provides X-ray Powder Diffraction (XRPD), Differential Scanning calorimetry (DSC) and Thermogravimetric Analysis (TGA) of ribociclib succinate. It further discloses the XRPD, DSC and TGA of ribociclib succinate after dynamic vapour sorption (DVS) (0-90-0% RH Cycle). WO 2012/064805 discloses that the non-hydrated form of ribociclib succinate is suitable for development. It is further mentioned that at 80% RH, 0.52% of the ribociclib succinate converts to hydrated form from the non-hydrated form.

In WO 2016/091221, the crystalline Form-I of ribociclib succinate is disclosed. Ribociclib succinate crystalline Form-I has characteristic peaks at 11.9°±0.2°, 19.4°±0.2°, 20.6°±0.2° in the X-ray powder diffraction pattern. WO 2016/091221 reports that Differential scanning calorimetry (DSC) of Form-I shows an endothermic peak at 197° C., while thermal gravimetric analysis (TGA) shows 2.0% weight loss at 178° C.

WO 2016/091221 further provides crystalline Form-A of ribociclib hemisuccinate characterized by X-ray powder diffraction pattern having characteristic peaks at 23.9°±0.2°, 20.0°±0.2°, 22.1°±0.2°. WO 2016/091221 reports that DSC data of Form-A shows an endothermic peak at 180° C., while TGA shows 12.5% weight loss at 118° C.

OBJECT OF THE INVENTION

It is an objective of the present invention to overcome the above-mentioned drawbacks of the prior art.

Another objective of the present invention is to provide an improved and commercially suitable process for the synthesis of ribociclib or its salts.

It is another objective of the present invention to provide a clean and green process for the preparation of a compound of formula A used in the synthesis of ribociclib or its salts.

It is another objective of the present invention to avoid tedious and long work-up procedures for the synthesis of ribociclib or its salts.

It is another objective of the present invention to provide novel polymoprhic forms of ribociclib succinate and ribociclib trifluoroacetate.

It is another objective of the invention to provide processes for the preparation of novel crystalline forms of ribociclib succinate and ribociclib trifluoroacetate.

It is yet another objective of the present invention to provide pharmaceutical compositions comprising a crystalline form selected from form M or N of ribociclib succinate for the treatment of a patient in need thereof.

SUMMARY OF THE INVENTION

In a first aspect, the present invention relates to a process for the preparation of a compound of formula V or a salt thereof.

Formula V

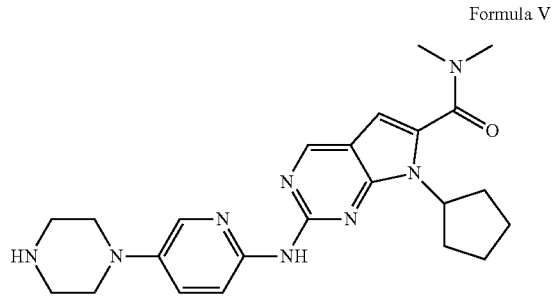 [SMILES: CN(C)C(=O)c1cc2cnc(Nc3ccc(N4CCNCC4)cn3)nc2n1C1CCCC1]

comprising the steps of:
a) reacting a compound of formula I,

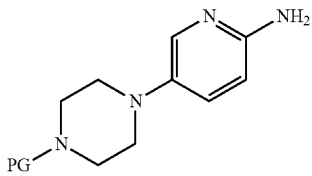

Formula I wherein PG is an amine protecting group;
with a compound of formula II,

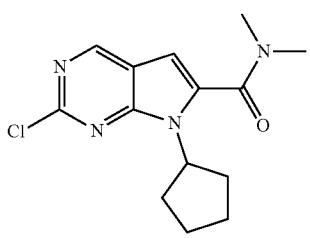

Formula II in the presence of a metal halide and a base to obtain a compound of formula III,

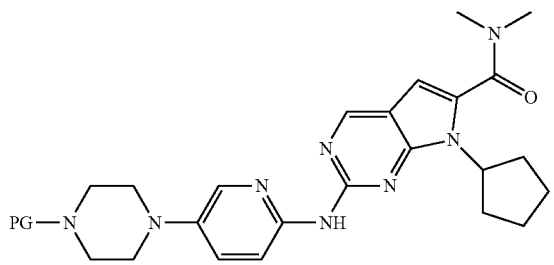

Formula III wherein PG is an amine protecting group;
b) de-protecting the compound of formula III to obtain an acid addition salt of a compound of formula IV,

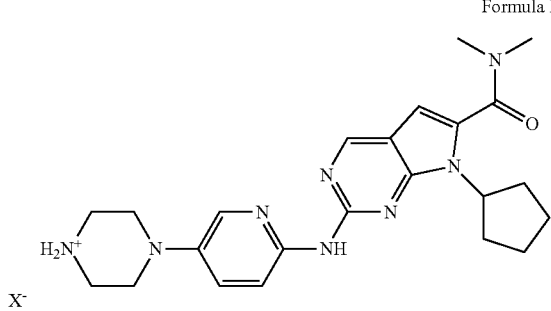

Formula IV wherein X⁻ is ion of the acid;
c) converting the compound of formula IV to obtain the compound of formula V,
d) optionally, converting the compound of formula V or a salt thereof.

Preferably, the acid addition salt of the compound of formula IV is the trifluoroacetic acid salt represented by the compound of formula IVa,

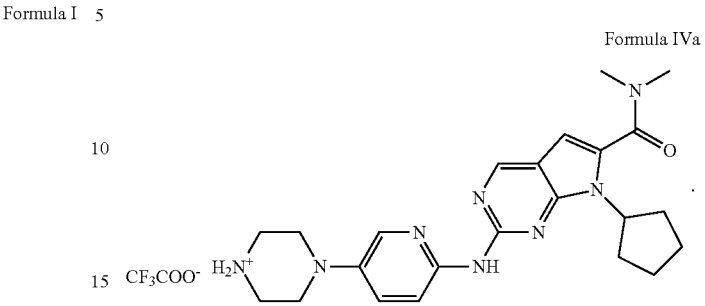

Formula IVa

Another aspect of the present invention is to provide a process for the preparation of a compound of formula I,

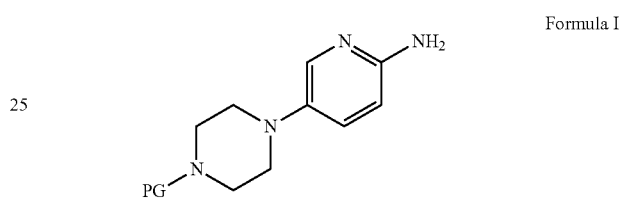

Formula I wherein PG is an amine protecting group;
comprising the reaction of compound of formula A,

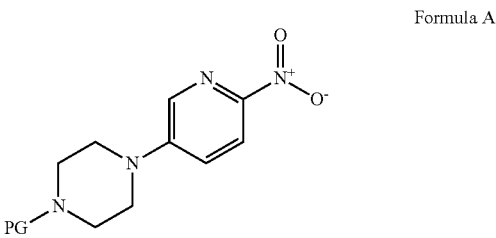

Formula A wherein PG is an amine protecting group;
with zinc and acetic acid, preferably in the presence of a solvent.

In another aspect, the present invention provides a crystalline Form-M of compound of formula VI, having characteristic X-ray powder diffraction peaks at an angle of refraction 2 theta 9.33, 18.83, 21.14, 21.37 and 23.10±0.2 degrees.

Another aspect of the present invention is to provide a process for the preparation of the crystalline Form-M of the compound formula VI, comprising the steps of:
i) dissolving the compound of formula V in an alcoholic solvent;
ii) adding succinic acid; and
iii) isolating the crystalline Form-M of formula VI.

The present invention further provides an alternative process for the preparation of the crystalline Form-M of compound of formula VI, comprising the steps of:
i) dissolving the compound of formula V in an alcoholic solvent;
ii) adding alcoholic solution of succinic acid;

iii) adding an aprotic solvent; and
iii) isolating a crystalline form-M of compound of formula VI.

In another aspect, the present invention provides a crystalline Form-N of compound of formula VI, having characteristic X-ray powder diffraction peaks at an angle of refraction 2 theta 4.68, 15.59, 15.70, 19.77 and 19.93±0.2 degrees.

Another aspect of the present invention is to provide a process for the preparation of the crystalline Form-N of formula VI, comprising the steps of:
i) dissolving the compound of formula V and succinic acid in a mixture of an aprotic and alcoholic solvent;
ii) adding aliphatic ether; and
iii) isolating the crystalline Form-N of formula VI.

25 The present invention further provides an alternative process for the preparation of the crystalline Form-N of compound of formula VI, comprising the steps of:
i) dissolving the compound of formula V and succinic acid in a mixture of an aprotic and alcoholic solvent;
ii) adding aliphatic ester; and
iii) isolating the crystalline Form-N of formula VI.

In another aspect, the present invention provides a crystalline Form-I of compound of formula IVa,

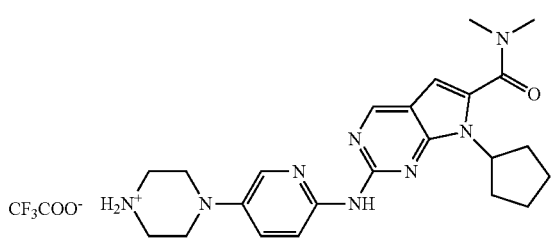

Formula IVa having characteristic X-ray powder diffraction peaks at an angle of refraction 2 theta 8.06, 8.11, 17.06, 20.33 and 22.02±0.2 degrees.

Another aspect of the present invention is to provide a process for the preparation of the crystalline Form-I of compound of formula IVa, comprising the steps of:
i) dissolving the compound of formula III in an aprotic solvent;

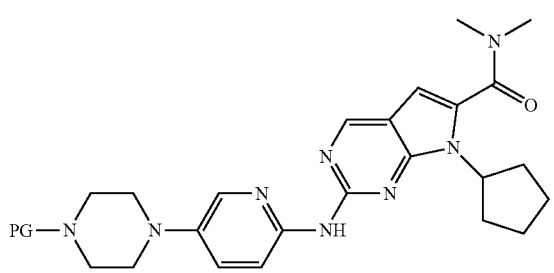

Formula III wherein PG is tert-butoxycarbonyl (Boc)
ii) adding trifluoroacetic acid;
iii) adding aliphatic ether; and
iv) isolating the crystalline Form-I of compound of formula IVa.

In another aspect, the present invention provides a pharmaceutical composition comprising a crystalline form of ribociclib succinate selected from crystalline form M or form N and at least one pharmaceutically acceptable excipient.

In yet another aspect, the invention relates to the use of such compositions in the treatment of a patient in need thereof, particularly for the treatment of postmenopausal women with hormone receptor (HR)-positive, human epidermal growth factor receptor 2 (HER2)-negative advanced or metastatic breast cancer.

DETAILED DESCRIPTION OF THE INVENTION

Definitions

Figure 1:
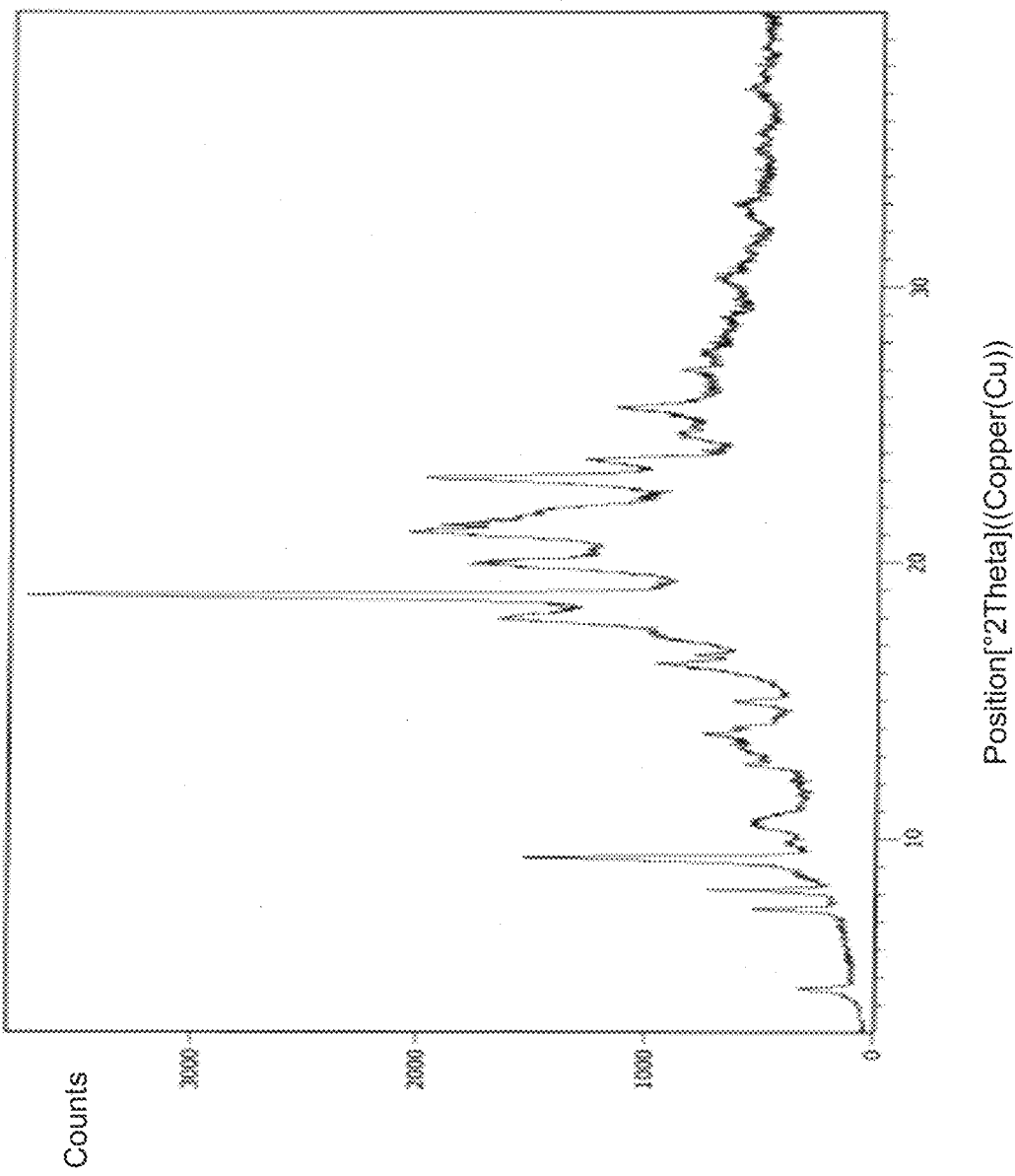
FIG. 1; represents an X-ray powder diffractogram of the crystalline Form-M of compound of formula VI of the present invention.

The following definitions are used in connection with the present application unless the context indicates otherwise.

The term "salt" of a compound relates to corresponding salt prepared by using acid selected from the group of mineral acids, such as hydrochloric acid, hydrobromic acid, phosphoric acid, metaphosphoric acid, nitric acid and sulphuric acid, and organic acids, such as tartaric acid, acetic acid, trifluoroacetic acid, citric acid, malic acid, lactic acid, fumaric acid, benzoic acid, glycolic acid, gluconic acid and succinic acid, and alkylsulphonic acids such as methanesulphonic, ethanesulphonic acids, ethane-1,2-di sulfonic acid and 2-hydroxyethanesulfonic acid and arylsulphonic acids such as benzene sulfonic acid, 2-naphthalenesulfonic acid, p-toluenesulphonic acid and naphthalene-1,5-disulfonic acid.

A particularly preferred salt of the compound of formula V is its succinate salt.

As used herein, the terms "comprising" and "comprises" mean the elements recited, or their equivalents in structure or function, plus any other element or elements which are not recited and the terms "comprising the steps of" include the steps recited, or the equivalent steps irrespective of the sequence in which they are recited.

The term "suitable solvent" means a solvent selected from the group of alcohols such as methanol, ethanol, t-butanol, n-butanol, isopropanol or the like or mixture thereof or halogenated hydrocarbons such as dichloromethane, chloroform, 1,2-dichloroethane or the like or mixture thereof or non-polar solvents such as benzene, toluene, dioxane, ethers, halogenated hydrocarbons such as dichloromethane, chloroform, 1,2-dichloroethane or the like or mixture thereof or polar aprotic solvents such as tetrahydrofuran, ethyl acetate, acetone, dimethylformamide, acetonitrile, dimethyl sulfoxide or the like or mixture thereof or polar protic solvents such as methanol, ethanol, t-butanol, n-butanol, isopropanol, formic acid, acetic acid, nitromethane or the like or mixture thereof or water or ketones such as acetone, diisobutyl ketone, cyclohexanone, methylcyclohexanone, methyl ethyl ketone, methyl isobutyl ketone, acetylacetone or the like or mixture thereof or esters such as methyl acetate, ethyl acetate or the like or mixture thereof or ethers such as dimethyl ether, methyl-t-butyl ether, diethyl ether, tetrahydrofuran, dioxane or the like or mixture thereof.

The term "amine protecting group PG" means groups introduced into a molecule at the nitrogen of the amine functionality in order to obtain chemoselectivity in the subsequent chemical reaction. Suitable amine function protection groups and protection and deprotection methods are well known in the art (see notably "Protective groups in organic synthesis", Greene T. W. and Wuts P. G. M., Wiley-Interscience, 1999). The suitable amine protecting group may be independently selected from tert-butyloxycarbonyl (Boc), phthaloyl, 9-fluorenylmethyloxycarbonyl (Fmoc), triphenylmethyl (Trityl), carboxybenzyl (Cbz), trifluoroacetyl, benzyl (Bn), benzylidene, methanesulfonyl (Mesyl), toluene sulfonyl (Tosyl) or acyl; the preferred protecting group being tert-butyloxycarbonyl (Boc).

The term "substantially free of impurity" refers to compounds with purity greater than 98% as measured by HPLC. More preferably, the compounds with purity greater than 99% as measured by HPLC and most preferably with purity greater than or equal to 99.6% as measured by HPLC.

In one aspect, the present invention relates to a process for the preparation of a compound of formula V or a salt thereof, Formula V comprising the steps of:
a) reacting a compound of formula I, Formula I wherein PG is an amine protecting group;
with a compound of formula II, Formula II in the presence of a metal halide and a base to obtain a compound of formula III,

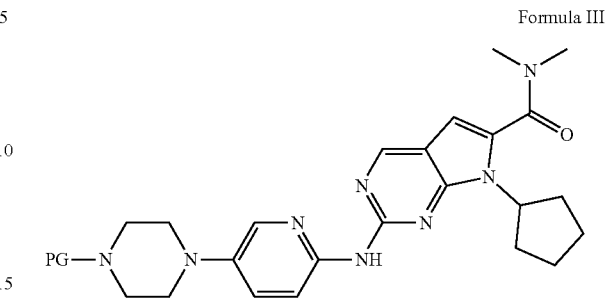

Formula III wherein PG is an amine protecting group;
b) de-protecting the compound of formula III to obtain an acid addition salt of formula IV, Formula IV wherein X⁻ is ion of the acid;
c) converting the compound of formula IV to the compound of formula V,
d) optionally, converting the compound of formula V to a salt.

The compounds of formula I and II as used in step a) may be prepared by methods known in the art, for example as disclosed in WO 2010/20675.

The metal halide may be selected from the group of copper (I) bromide, copper (I) iodide and copper (I) chloride. Preferably, the metal halide is copper (I) iodide.

The base may be selected from the group of inorganic or organic base such as sodium hydride, lithium hydride, sodium hydroxide, sodium methoxide, lithium methoxide, butyl lithium, potassium tertiary butoxide, quarternary ammonium bases, triethylamine, triisobutylamine, N,N-diisopropylethylamine (DIPEA), N,N-dimethylaniline, N-methylmorpholine, N-methylpyrrolidine, pyridine or combinations thereof. Preferably, the base is selected from sodium hydride and potassium tertiary butoxide. Most preferably, the base is sodium hydride. Also preferably, the base is potassium tertiary butoxide.

In one embodiment, the reaction of the compound of formula I with the compound of formula II in step a) is carried out in the presence of a suitable solvent. More preferably, the suitable solvent is selected from the group of tetrahydrofuran, ethyl acetate, acetone, dimethylformamide, acetonitrile, dimethyl sulfoxide. Most preferably, the solvent is acetonitrile.

Preferably, the step a) wherein the compound of formula I is reacted to the compound of formula II in the presence of a metal halide is carried out at room temperature. Subsequently, the reaction mixture is preferably stirred for 1 to 2 hours at 40-80° C. Most preferably, the reaction mixture is stirred at 70-80° C. under nitrogen atmosphere for 1 to 2 hours.

In a preferred embodiment, a compound of formula Ia is reacted with the compound of formula II, in the presence of copper (I) iodide, sodium hydride and acetonitrile at 20-30° C. Preferably, the reaction mixture is stirred for 1 to 2 hours at 70-80° C. under nitrogen atmosphere to obtain the compound of formula IIIa.

The compound of formula V or a salt thereof, may also be prepared by reacting the compound of formula I with a compound of formula II in the presence of a base without using any catalyst or a metal halide.

The compound of formula IIIa is isolated as a solid by adding a suitable solvent selected from group of polar solvents such as methanol, ethanol, t-butanol, n-butanol, isopropanol, water or the like or mixture thereof. Preferably, the solvent is selected from methanol and water or a mixture thereof.

In an embodiment, the compound of formula IIIa is isolated as a solid by adding water to the reaction mixture.

In another embodiment, the compound of formula IIIa is isolated as a solid by adding methanol and water to the reaction mixture.

Preferably, purity of the isolated compound of formula IIIa is at least 99.0%, e.g., at least 99.2%, at least 99.5%, or at least 99.7% as measured by HPLC. Preferably, the reaction yield is at least 50%, e.g., at least 55%, at least 60%, or at least 65%.

The above mentioned process makes isolation of the compounds of formula III very easy. This avoids tedious work up procedures including column chromatography or quenching with an acidic or basic solution.

The inventors of the present invention have found that the isolation of the compound of formula III as a solid material at this stage is advantageous as it reduces the amount of impurities.

Thus the present invention has the advantages of providing the compound of formula III in a high yield and substantially free of impurities.

The methods for the preparation of the compound of formula III reported in the prior art involve organophosphorus and palladium compounds such as (2,2'-bis(diphenylphosphino)-1,1'-binaphthyl (BINAP) and Palladium(II) acetate. These methods require tedious and long work-up procedures including column chromatography.

The acid addition salt of formula IV is prepared by de-protection of the compound of formula III, preferably by cleaving off the protecting group PG using standard conditions for the deprotection of amines. Preferably, a suitable organic or inorganic acid such as hydrochloric acid, nitric acid, sulfuric acid, phosphoric acid, formic acid, acetic acid, citric acid, trifluoroacetic acid, p-toluenesulfonic acid and the like is used, preferably in a suitable solvent; preferably tetrahydrofuran, ethyl acetate, dichloromethane or acetonitrile.

The X⁻ in formula IV is anion of organic or an inorganic acids such as hydrochloric acid, hydrobromic acid, phosphoric acid, metaphosphoric acid, nitric acid and sulphuric acid, tartaric acid, acetic acid, trifluoroacetic acid, citric acid, malic acid, lactic acid, fumaric acid, benzoic acid, glycolic acid, gluconic acid, succinic acid, methanesulphonic, ethanesulfonic acids, ethane-1,2-disulfonic acid, 2-hydroxyethanesulfonic acid, benzene sulfonic acid, 2-naphthalenesulfonic acid, p-toluenesulfonic acid and naphthalene-1,5-disulfonic acid.

The deprotection may be carried out using from 1 to 10 equivalents of acid, more preferably from 1 to 3 equivalents at reduced or elevated temperatures, for example from −30° C. to 40° C., more preferably from 5 to 10° C., over a time period ranging from 1 minute to 10 hours, more preferably from 4 to 6 hours.

In a preferred embodiment of the present invention, the trifluoroacetic acid salt of formula IVa,

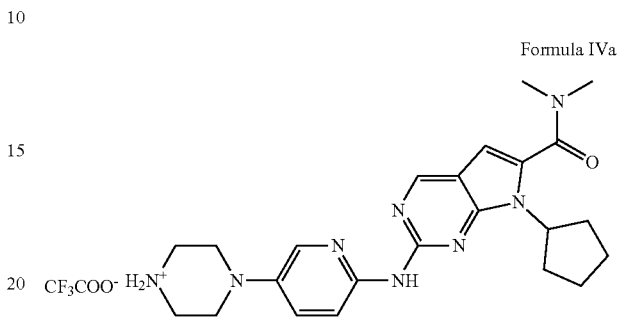

Formula IVa is prepared by treating a compound of formula IIIa with trifluoroacetic acid, optionally in the presence of a suitable solvent such as dichloromethane. The reaction mixture is stirred for 4 to 6 hours, at 20 to 30° C. To the reaction mixture an ether solvent such as methyl-t-butyl ether is added followed by stirring for 2 to 3 hours at 15 to 30° C. The obtained solid is filtered and dried to obtain the compound of formula IVa.

The conversion of compound of formula IV or IVa to the compound of formula V may be carried out in the presence of a base to obtain the compound of formula V or a salt thereof,

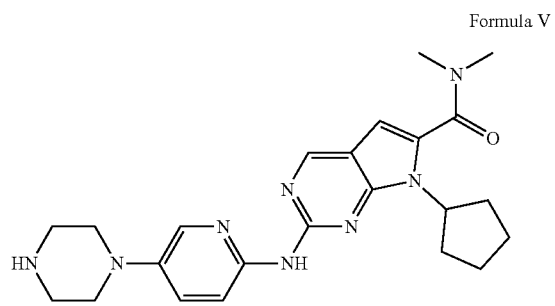 [SMILES: CN(C)C(=O)c1cc2cnc(Nc3ccc(N4CCNCC4)cn3)nc2n1C1CCCC1]

Formula V

The base may be selected from the group of inorganic or organic base such as sodium hydride, lithium hydride, sodium hydroxide, sodium methoxide, lithium methoxide, butyl lithium, potassium tertiary butoxide, quarternary ammonium bases, triethylamine, triisobutylamine, N,N-diisopropylethylamine (DIPEA), N,N-dimethylaniline, N-methylmorpholine, N-methylpyrrolidine, pyridine or combinations thereof. Preferably, the base is an inorganic base. Most preferably, the base is sodium hydroxide.

Preferably, the reaction is carried out in the presence of a suitable solvent. More preferably, the suitable solvent may be selected from the group of polar solvents such as methanol, ethanol, t-butanol, n-butanol, isopropanol, water or the like or mixture thereof. Most preferably, the reaction is carried out in the presence of water.

In a preferred embodiment, the compound of formula V is prepared by reacting a compound of formula IV or IVa with an inorganic base such as sodium hydroxide, optionally in the presence of a suitable solvent such as water. The reaction mixture is stirred for 4 to 6 hours. The obtained solid is dried at 40 to 60° C. to give the compound of formula V.

The succinate salt of the compound of formula V is represented by formula VI,

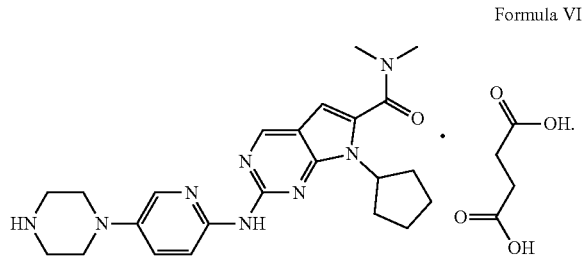

Formula VI

The compound of formula VI may be prepared by using the methods disclosed in the art. For example, the compound of formula VI can be prepared by reacting the compound of formula V with succinic acid in the presence of 2-propanol. Such a process is, for example, disclosed in WO 2012/064805.

In a preferred embodiment of the present invention, the compound of formula VI is prepared by dissolving the compound of formula V in a suitable solvent such as methanol or a mixture of suitable solvents such as methanol and dichloromethane followed by addition of succinic acid or a solution of succinic acid in a suitable solvent such as methanol at 20 to 70° C. Preferably, the reaction mixture is cooled to 20 to 30° C. and stirred for 2 to 4 hours to give the compound of formula VI.

Another aspect of the present invention is to provide a process for the preparation of a compound of formula I,

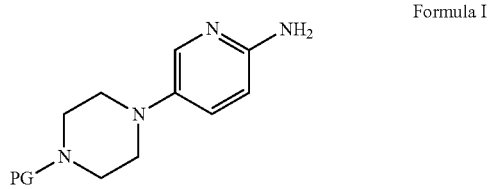

Formula I wherein PG is an amine protecting group;
comprising the reaction of a compound of formula A,

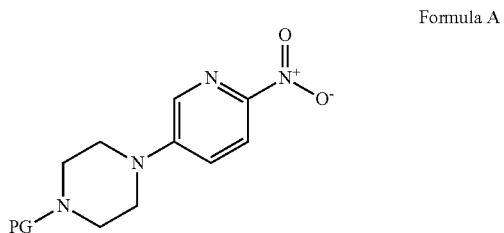

Formula A wherein PG is an amine protecting group;
with zinc and acetic acid.

The compound of formula A can be prepared by methods known in the art, for example by a process as disclosed in WO 2012/064805 or WO2010/20675 where 5-halo-2-nitropyridine is reacted with piperazine to obtain the compound of formula A.

Preferably, the compound of formula A is prepared by reacting a compound of formula B,

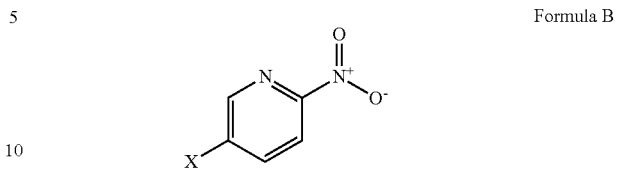

Formula B wherein X is selected from bromo and chloro;
with a compound of formula C,

Formula C wherein PG is an amine protecting group;
in a green solvent such as water in the presence of a base.
In some embodiments, the base is selected from the group consisting of sodium carbonate, potassium carbonate, diethylamine, N,N-diisopropylethylamine and mixtures thereof. In certain embodiments, the base is sodium carbonate. In some embodiments, the reaction is carried out at 85° C. to 110° C.

In certain preferred embodiments, the compound of formula A wherein PG is BOC is prepared by reacting 5-bromo-2-nitropyridine with N-BOC-piperazine in water in the presence of sodium carbonate at 90 to 100° C.

The process for the preparation of compound of formula A or Aa has the advantage that the reaction is carried in a green solvent such as water. This process does not require the use of any hazardous solvent or any special reagent during the reaction. The process of the present invention is environmental-friendly, simple, cost effective and, therefore, attractive at a commercial scale.

Preferably, the reaction of the compound of formula A with zinc and acetic acid is carried out in the presence of a suitable solvent. More preferably, the suitable solvent may be selected from the group of polar solvents such as methanol, ethanol, t-butanol, n-butanol, isopropanol, water or the like or mixture thereof. Most preferably, the reaction is carried out in the presence of water.

Preferably, the reaction is carried out at 0 to 30° C., most preferably at 10 to 20° C.

In a preferred embodiment, the reaction of the compound of formula Aa with zinc and acetic acid is carried out in the presence of water at 10 to 20° C. The reaction mixture is stirred for 2 to 3 hours at the same temperature to obtain the compound of formula Ia. Preferably, the compound of formula Ia is isolated by adding dichloromethane to the reaction mixture followed by filtration through celite pad. Typically, the dichloromethane layer is concentrated under vacuum to obtain the compound of formula Ia as a solid.

The present invention also has the advantage of providing the compound of formula Ia in a high yield and substantially free of impurities. Preferably, the reaction yield is at least 75%, e.g., at least 80%, at least 85%, or at least 89%, and the purity is at least 99.0%, e.g., at least 99.3%, at least 99.6%, or at least 99.9%, as measured by HPLC.

The methods known in the art involve tedious work up procedures, such as column chromatography, which makes the process less attractive at commercial scale. On the other hand, the process of the present invention simplifies the isolation of the compounds of formula I.

In another aspect, the present invention provides a crystalline Form-M of compound of formula VI, having characteristic X-ray powder diffraction peaks at an angle of refraction 2 theta 9.33, 18.83, 21.14, 21.37 and 23.10±0.2 degrees.

In an embodiment, the crystalline Form-M of compound of formula VI is characterised by X-ray powder diffraction peaks at an angle of refraction 2 theta 4.59, 9.19, 9.33, 13.78, 18.02, 18.83, 19.98, 21.14, 21.37 and 23.10±0.2 degrees.

In a preferred embodiment, the crystalline Form-M of compound of formula VI is characterised by X-ray powder diffraction chromatograph as shown in FIG. 1.

In another embodiment, the crystalline Form-M of compound of formula VI is characterised by a DSC thermogram with two endothermic peaks at about 179 and 182.45° C.

Another aspect of the present invention is to provide a process for the preparation of a crystalline Form-M of compound formula VI, comprising the steps of:
  i) dissolving the compound of formula V in an alcoholic solvent;
  ii) adding succinic acid; and
  iii) isolating the crystalline form-M of formula VI.

The alcoholic solvent may be selected from the group of substituted or un-substituted straight chain, branched chain, cyclic or aromatic alcohols such as methanol, ethanol, n-propanol, iso-propanol, cyclopentanol, cyclohexanol or benzyl alcohol, preferably, the alcoholic solvent is methanol.

In an embodiment, the compound of formula V is dissolved in an alcoholic solvent at a temperature of 50 to 70° C. to obtain a clear solution. To this solution, succinic acid is added at the same temperature. The reaction mixture is cooled to 20 to 30° C. and stirred for 2 to 4 hours. The solid material is filtered and dried under vacuum to obtain crystalline Form-M of the compound of formula VI.

In a preferred embodiment, the compound of formula V is dissolved in methanol at 50 to 70° C., more preferably at 60 to 65° C. to obtain a clear solution. To this solution, succinic acid is added at the same temperature. The reaction mixture is cooled to 20 to 30° C. and stirred for 2 to 4 hours. The solid material is filtered and dried under vacuum to obtain crystalline Form-M of compound of formula VI.

In another aspect the present invention provides an alternative process for the preparation of a crystalline form-M of compound of formula VI, comprising the steps of:
  i) dissolving the compound of formula V in an alcoholic solvent;
  ii) adding alcoholic solution of succinic acid;
  iii) adding an aprotic solvent;
  iii) isolating a crystalline form-M of compound of formula VI.

The alcoholic solvent may be selected from the group of substituted or un-substituted straight chain, branched chain, cyclic or aromatic alcohols such as methanol, ethanol, n-propanol, iso-propanol, cyclopentanol, cyclohexanol or benzyl alcohol, preferably, the alcoholic solvent is methanol.

The aprotic solvent may be selected from the group of tetrahydrofuran, ethyl acetate, acetone, dimethylformamide, acetonitrile, dimethyl sulfoxide and the like. Preferably, the aprotic solvent is acetone.

In an embodiment, the compound of formula V is dissolved in an alcoholic solvent at room temperature to obtain a clear solution. To this solution alcoholic solution of succinic acid is added at same temperature and the reaction mixture is stirred for 1 to 2 hours. To the reaction mixture aprotic solvent is added, cooled to room temperature and stirred for 2 to 4 hours. The solid material is filtered and dried under vacuum give crystalline Form-M of the compound of formula VI.

In a preferred embodiment, the compound of formula V is dissolved in methanol at 50 to 70° C., more preferably at 60 to 65° C. to obtain a clear solution. To this solution, methanolic solution of succinic acid is added and stirred at same temperature for 1 to 2 hours. To this reaction mixture acetone is added and cooled to room temperature. The reaction mixture is stirred for 2-4 hours and solid material is filtered and dried to give crystalline Form-M of the compound of formula VI.

In another aspect, the present invention provides a crystalline Form-N of compound of formula VI, having characteristic X-ray powder diffraction peaks at an angle of refraction 2 theta 4.68, 15.59, 15.70, 19.77 and 19.93±0.2 degrees.

In an embodiment, the crystalline Form-N of compound of formula VI is characterised by X-ray powder diffraction peaks at an angle of refraction 2 theta 4.68, 6.36, 7.52, 15.59, 15.70, 19.42, 19.77, 19.93, 20.21 and 21.27±0.2 degrees.

Figure 2:
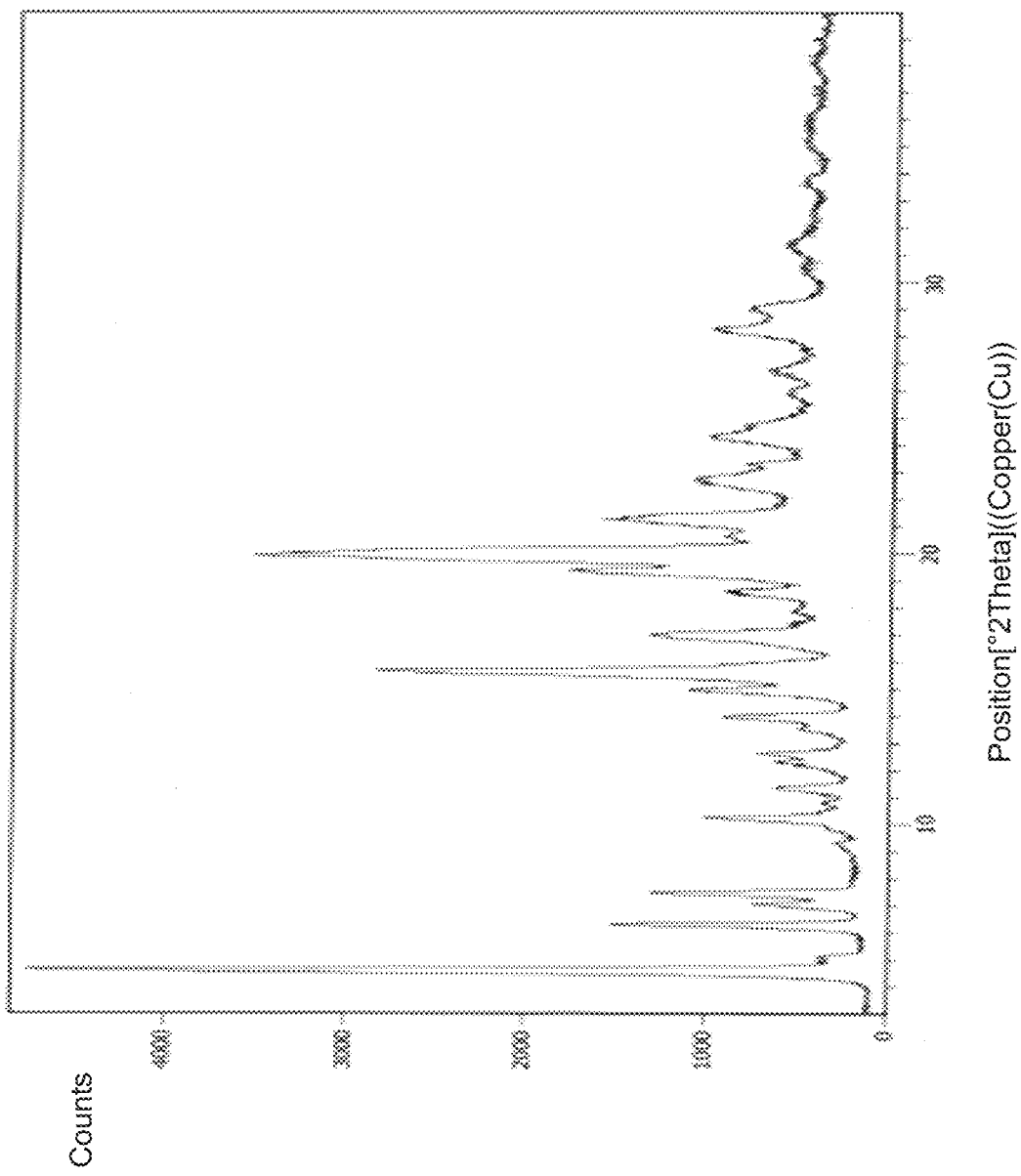
FIG. 2; represents an X-ray powder diffractogram of the crystalline Form-N of compound of formula VI of the present invention.

In a preferred embodiment, the crystalline Form-N of compound of formula VI is characterised by X-ray powder diffraction chromatograph as shown in FIG. 2.

In another embodiment, the crystalline Form-N of compound of formula VI is characterised by characterized by a DSC thermogram with an endothermic peak at about 185.26° C.

Another aspect of the present invention is to provide a process for the preparation of a crystalline Form-N of formula VI comprising the steps of:
  i) dissolving the compound of formula V and succinic acid in a mixture of an aprotic and alcoholic solvent,
  ii) adding aliphatic ether, and
  iii) isolating a crystalline form-N of formula VI.

The present invention further provides another process for the preparation of the crystalline Form-N of compound of formula VI, comprising the steps of:
  i) dissolving the compound of formula V and succinic acid in a mixture of an aprotic and alcoholic solvent;
  ii) adding aliphatic ester; and
  iii) isolating the crystalline Form-N of formula VI.

The alcoholic solvent may be selected from the group of substituted or un-substituted straight chain, branched chain, cyclic or aromatic alcohols such as methanol, ethanol, n-propanol, iso-propanol, cyclopentanol, cyclohexanol or benzyl alcohol, preferably, the alcoholic solvent is methanol.

The aprotic solvent may be selected from the group of tetrahydrofuran, ethyl acetate, acetone, dimethylformamide, acetonitrile, dichloromethane, dimethyl sulfoxide and the like, preferably, the aprotic solvent is dichloromethane.

The aliphatic ether may be selected from the group of dimethyl ether, diethyl ether, di-isopropyl ether, methyl-t-butyl ether and the like, preferably, the aliphatic ether is di-isopropyl ether.

In an embodiment, the compound of formula V and succinic acid is dissolved in a mixture of an aprotic and alcoholic solvent and stirred for 1-2 hours. To the reaction mixture, aliphatic ether is added and reaction mixture is stirred for 4-5 hours. The solid material is filtered and dried under vacuum give crystalline Form-N of the compound of formula VI.

In a preferred embodiment, the compound of formula V and succinic acid is dissolved in a mixture of dichloromethane and methanol at room temperature and stirred for 1-2 hours to obtain a clear solution. To the solution, di-isopropyl ether is added and stirred at same temperature for 4-5 hours.

The solid material is filtered and dried to give crystalline Form-N of the compound of formula VI.

In another aspect, the present invention provides a crystalline Form-I of the compound of formula IVa,

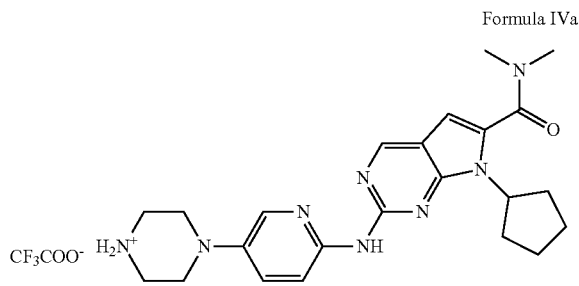 [SMILES: "CF3COO-" ; CN(C)C(=O)c1cc2cnc(Nc3ccc(N4CC[NH2+]CC4)cn3)nc2n1C1CCCC1]

Formula IVa having characteristic X-ray powder diffraction peaks at an angle of refraction 2 theta 8.06, 8.11, 17.06, 20.33 and 22.02±0.2 degrees.

In an embodiment, the crystalline Form-I of compound of formula IVa is characterised by X-ray powder diffraction peaks at an angle of refraction 2 theta 5.02, 6.55, 8.06, 8.11, 10.44, 16.23, 17.06, 19.96, 20.33 and 22.02±0.2 degrees.

Figure 3:
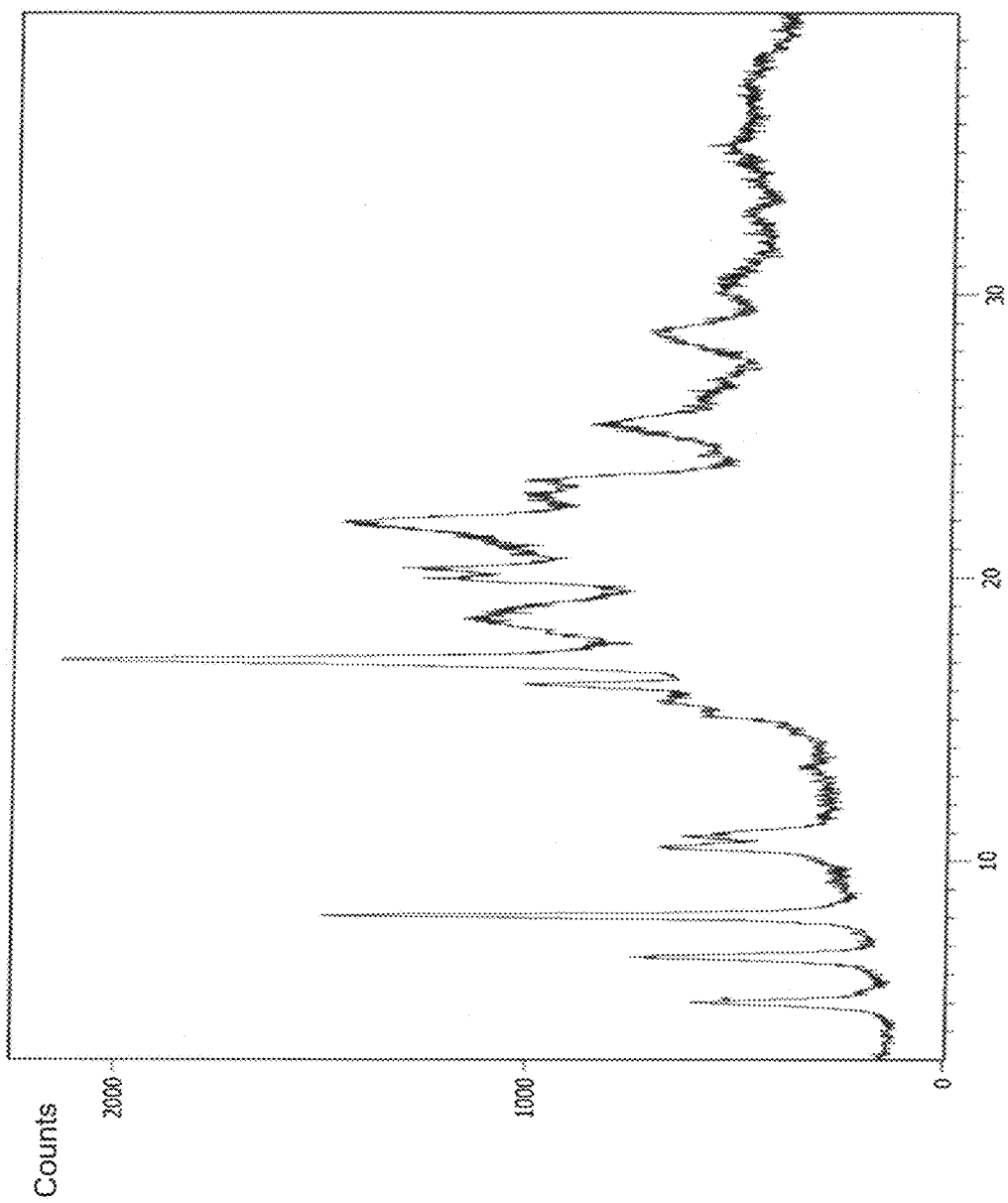
FIG. 3; represents an X-ray powder diffractogram of the crystalline Form-I of compound of formula IVa, wherein X is trifluoroacetate of the present invention.

In a preferred embodiment, the crystalline Form-I of compound of formula IVa is characterised by X-ray powder diffraction chromatograph as shown in FIG. 3.

Another aspect of the present invention is to provide a process for the preparation of a crystalline Form-I of the compound of formula IVa, comprising the steps of:
i) dissolving the compound of formula III in an aprotic solvent, Formula III wherein PG is an amine protecting group;
ii) adding trifluoroacetic acid,
iii) adding aliphatic ether, and
iv) isolating the crystalline form-I of compound of formula IVa.

The aprotic solvent may be selected from the group of tetrahydrofuran, ethyl acetate, acetone, dimethylformamide, acetonitrile, dichloromethane, dimethyl sulfoxide and the like. Preferably, the aprotic solvent is dichloromethane.

The aliphatic ether may be selected from the group of dimethyl ether, diethyl ether, di-isopropyl ether, methyl-t-butyl ether and the like. Preferably, the aliphatic ether is methyl-t-butyl ether.

In an embodiment, the compound of formula III is dissolved in an aprotic solvent. To this solution, trifluoroacetic acid is added at −5 to 25° C. The reaction mixture is stirred for 4-5 hours at 10 to 35° C. To the reaction mixture, aliphatic ether is added at same temperature and reaction mixture was stirred for 2-3 hours. The solid material is filtered and dried under vacuum give crystalline Form-I of the compound of formula IVa.

In a preferred embodiment, the compound of formula IIIa is dissolved in dichloromethane. To this solution, trifluoroacetic acid is added at −5 to 25° C., more preferably at 5-10° C. The reaction mixture is stirred for 4-5 hours at 10 to 35° C., more preferably at 15 to 25° C. To the reaction mixture, methyl-t-butyl ether is added at same temperature and reaction mixture was stirred for 2-3 hours. The solid material is filtered and dried under vacuum give crystalline Form-I of the compound of formula IVa.

The crystalline forms of the present invention may be isolated from the reaction mixture by any of the suitable techniques such as precipitation, decantation, centrifugation, evaporation, distillation and filtration or combinations thereof.

In another aspect, the present invention provides a pharmaceutical composition comprising a crystalline form of ribociclib succinate selected from crystalline form M or form N and at least one pharmaceutically acceptable excipient.

In yet another aspect, the invention relates to the use of such compositions in the treatment of a patient in need thereof, particularly for the treatment of postmenopausal women with hormone receptor (HR)-positive, human epidermal growth factor receptor 2 (HER2)-negative advanced or metastatic breast cancer.

EXPERIMENTAL

Detailed experimental parameters according to the present invention are provided by the following examples, which are intended to be illustrative and not limiting of all possible embodiments of the invention.

Instruments

XRD

The X-ray Powder Diffraction (XRPD): XRPD analysis was conducted on a Panalytical, Model-Empyrean X-Ray powder diffractometer. The instrumental parameters are mentioned below.

| | |
|---|---|
| Start position [°2Theta] | 3.0 |
| End position [°2Theta] | 40.0 |
| Step size [°2Theta] | 0.013 |
| Scan step time (s) | 39.27 |
| Anode material | Cu |
| Generator setting | 40 mA, 45 KV |
| Spinning | Yes |
| Goniometer | theta: theta |
| Sample stage | Reflection-transmission spinner |
| Sample mode | Reflection |
| Sample specimen preparation | Sample back loading technique |

DSC

The thermal analysis of Ribociclib was conducted by differential scanning calorimetry (DSC) (TA Instruments-DSC Q-2000) equipped with refrigerated cooling system (RCS90). Analysis was performed by taking 1 to 2 mg of sample into low mass aluminium sample pan with lid. The thermogram was recorded as per following methodology
1. Equilibrate at 25° C.
2. Ramp 10° C. to 300° C.
3. Nitrogen flow 50 ml/min

NMR

NMR spectra (1H, 13C) were recorded on Varian 400 MHz NMR using $CDCl_3$ as the solvent.

EXAMPLES

Example-1

Preparation of tert-butyl 4-(6-nitropyridin-3-yl) piperazine-1-carboxylate

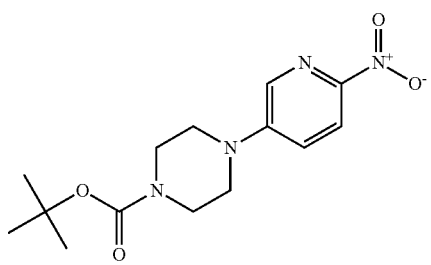 [SMILES: CC(C)(C)OC(=O)N1CCN(c2ccc([N+](=O)[O-])nc2)CC1]

Method-1

Piperazine (85 g) and 5-Bromo-2-nitropyridine (100 g) were added in DMF and cooled to 50-60° C., followed by addition of 2-propanol (1000 ml) and stirred for 1 hr. The reaction mixture was further cooled to 20-30° C. and stirred for 2-3 hrs. The reaction mass was filtered under vacuum and washed with 2-propanol. The resulting solid was treated with Boc anhydride (161 g) in the presence of diisopropyl ethyl amine (95 g) in dichloromethane (500 ml) at ambient temperature. Product was isolated by addition of n-heptane (1200 mL) followed by filtration and washing with n-heptane and dried under vacuum at 50-60° C. to give pale yellow solid (130 g).

Yield: 85.0%; HPLC Purity: 99.0%

Method-2

Piperazine (85 g) and 5-Bromo-2-nitropyridine (100 g) were added in acetonitrile at room temperature. The reaction mixture was heated to 70-80° C. for 12-15 hrs.

The reaction mass was concentrated under vacuum followed by addition of 2-propanol (1000 ml) and stirred for 1 hr at 50-60° C. The reaction mixture was further cooled to 20-30° C. and stirred for 2-3 hrs. The reaction mass was filtered under vacuum and washed with 2-Propanol. The resulting solid was treated with Boc anhydride (161 g) in the presence of diisopropyl ethyl amine (95 g) in acetonitrile (500 ml) at ambient temperature. Product was isolated by addition of distilled water (500 mL) followed by filtration and washing and dried under vacuum at 50-60° C. to give pale yellow solid (130 g).

Yield: 85.0%; HPLC Purity: 99.0%

$^1$H NMR (400 MHz CDCl3) δ ppm 8.18-8.16 (d, J=9.2, 1H), 8.13-8.12 (d, J=2.8, 1H), 7.22-7.19 (dd, J1=3.2, J2=9.6, 1H), 3.64 (t, 4H), 3.45 (t, 4H), 1.48 (s, 9H).

Method-3

To a mixture of 5-Bromo-2-nitropyridine (50 g), N-Boc-piperazine (68.8 g) and sodium carbonate (183.3 g) 500 mL distilled water added. The reaction mixture was heated at 90-100° C. under stirring for 8-10 hrs. The reaction mixture was cooled to 20-30° C. Distilled water and n-heptane (250 mL) was added to the reaction mixture. The solid obtained was collected by filtration.

Example-2

Preparation of tert-butyl 4-(6-aminopyridin-3-yl) piperazine-1-carboxylate

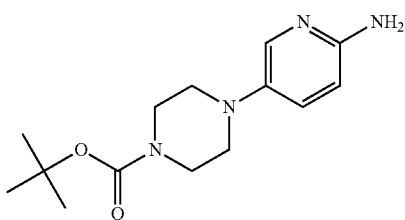 [SMILES: CC(C)(C)OC(=O)N1CCN(c2ccc(N)nc2)CC1]

To the mixture of tert-butyl 4-(6-nitropyridin-3-yl) piperazine-1-carboxylate (100 g) and zinc dust (100 g) in 500 ml of DM water was added acetic acid (300 ml) at 10-20° C. The reaction mixture was stirred over 2 hrs at 10-20° C. Dichloromethane was added to reaction mixture followed by celite bed filtration to remove excess zinc. Layer was separated out followed by washing of organic layer with 15% Potassium Carbonate solution. The organic layer was concentrated under vacuum and added n-heptane (1000 mL). Reaction mixture was stirred for 2-3 hrs at 20-30° C. The solid was collected by filtration to give tan solid (80 g).

Yield: 89.0%; HPLC Purity: 100.0%

$^1$H NMR (400 MHz CDCl3) δ ppm 7.77 (d, J=2.8, 1H), 7.17-7.14 (dd J1=9.2, J2=3.2, 1H), 6.49-6.47(d, J=8.0, 1H), 4.24 (br, 2H), 3.56 (t, 4H), 2.97 (t, 4H), 1.48 (s, 9H).

Example-3

Preparation of tert-butyl 4-(6-{[7-cyclopentyl-6-(dimethyl carbamoyl)-7H-pyrrolo[2,3-d]pyrimidin-2-yl]amino}pyridin-3-yl) piperazine-1-carboxylate

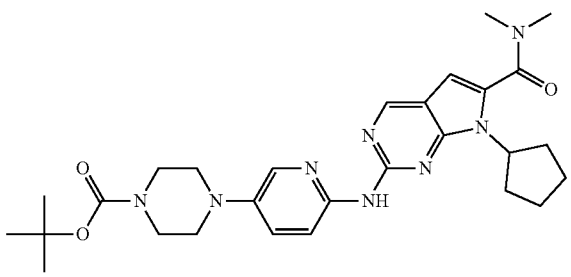 [SMILES: CN(C)C(=O)c1cc2cnc(Nc3ccc(N4CCN(C(=O)OC(C)(C)C)CC4)cn3)nc2n1C1CCCC1]

Method-1

To the solution of tert-butyl 4-(6-aminopyridin-3-yl) piperazine-1-carboxylate (100 g) and 2-chloro-7-cyclopentyl-N,N-dimethyl-7H-pyrrolo[2,3-d]pyrimidine-6-carboxamide (100 g) in acetonitrile (1000 ml) was added sodium hydride (34 g) and copper (I) iodide (3.25 g) at 20-30° C. The reaction mixture was placed under nitrogen for 1 hr at 70-80° C. After completion of the reaction, methanol (50 ml) was added followed by addition of distilled water. The reaction mass was slowly cooled to 20-30° C. and stirred for 2-3 hrs. The solid was collected by filtration to give off white to light grey solid (125 g).

Yield: 65.0%; HPLC Purity: 99.7%

¹H NMR (400 MHz CDCl3) δ ppm 8.70 (s, 1H), 8.38-8.36 (d, J=9.2, 1H), 8.02 (d, J=2.4, 2H), 7.35-7.32 (dd, J=3.2, J=9.2, 1H), 6.43(s, 1H), 4.81-4.74 (m, 1H), 3.61(t, 4H), 3.15 (s, 6H), 3.09 (t, 4 H), 2.62-2.53 (m, 2H), 2.08-2.0 (m, 4H), 1.75-1.64 (m, 2H), 1.49 (s, 9H).

Method-2

To the solution of tert-butyl 4-(6-aminopyridin-3-yl) piperazine-1-carboxylate (100 g) and 2-chloro-7-cyclopentyl-N,N-dimethyl-7H-pyrrolo[2,3-d]pyrimidine-6-carboxamide (100 g) in acetonitrile (1000 ml) was added potassium tertiary butoxide (76.65 g) and copper (I) iodide (3.25 g) at 20-30° C. The reaction mixture was placed under nitrogen for 1 hr at 70-80° C. After completion of the reaction, distilled water (1000 ml) was added. The reaction mass was slowly cooled to 20-30° C. under stirring for 2-3 hrs and filtered to give off white to light grey solid (125 g).

Yield: 65.0%; HPLC Purity: 99.7%

Example 4 a. Preparation of 4-(6-{[7-cyclopentyl-6-(dimethylcarbamoyl)-7H-pyrrolo[2,3-d]pyrimidin-2-yl]amino}pyridin-3-yl)piperazin-1-ium trifluoroacetate

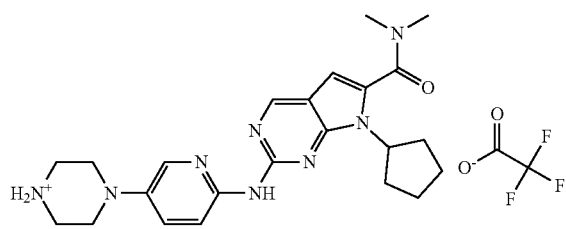 [SMILES: CN(C)C(=O)c1cc2cnc(Nc3ccc(N4CC[NH2+]CC4)cn3)nc2n1C1CCCC1 ; O=C([O-])C(F)(F)F]

To the solution of tert-butyl 4-(6-{[7-cyclopentyl-6-(dimethyl carbamoyl)-7H-pyrrolo[2,3-d]pyrimidin-2-yl]amino}pyridin-3-yl)piperazine-1-carboxylate (64 g) in 128 ml of DCM was added TFA (128 ml) at 5-10° C. The solution was stirred over 4 hrs at 20-25° C. To this was added methyl tertiary butyl ether (320 ml) and stirred for 1 hr at 20-25° C.

The solid was collected by filtrations to give 4-(6-{[7-cyclopentyl-6-(dimethylcarbamoyl)-7H-pyrrolo[2,3-d]pyrimidin-2-yl]amino}pyridin-3-yl)piperazin-1-ium-trifluoroacetate salt.

b. Preparation of Form-I (FIG. 3) of 4-(6-{[7-cyclopentyl-6-(dimethyl carbamoyl)-7H-pyrrolo[2,3-d] pyrimidin-2-yl]amino}pyridin-3-yl) piperazin-1-ium trifluoroacetate To the solution of tert-butyl 4-(6-{[7-cyclopentyl-6-(dimethylcarbamoyl)-7H-pyrrolo[2,3-d]pyrimidin-2-yl]amino}pyridin-3-yl)piperazine-1-carboxylate (6.0 g) in 15 ml of DCM was added TFA (15 ml) at 5-10° C. The solution was stirred over 3-4 hrs at 20-30° C. To this was added methyl tertiary butyl ether (60 ml) and stirred for 2-3 hrs at 15-25° C. The solid was collected by filtration followed by drying at 40-50° C. to give crystalline form I of 4-(6-{[7-cyclopentyl-6-(dimethylcarbamoyl)-7H-pyrrolo[2,3-d]pyrimidin-2-yl]amino}pyridin-3-yl)piperazin-1-ium-trifluoro acetate (100 g).

Yield: 99.0%; HPLC Purity: 99.8%

Example 5

Preparation of 7-cyclopentyl-N,N-dimethyl-2-{[5-(piperazin-1-yl)pyridin-2-yl]amino}-7H-pyrrolo[2,3-d]pyrimidine-6-carboxamide

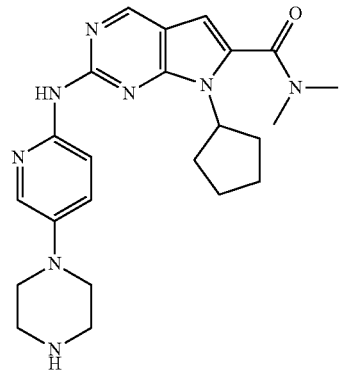 [SMILES: CN(C)C(=O)c1cc2cnc(Nc3ccc(N4CCNCC4)cn3)nc2n1C1CCCC1]

Method-1

To a solution of 4-(6-{[7-cyclopentyl-6-(dimethylcarbamoyl)-7H-pyrrolo[2,3-d] pyrimidin-2-yl]amino}pyridin-3-yl) piperazin-1-ium trifluoroacetate (100 g) in 2500 ml of distilled water was added 20% sodium hydroxide solution and adjusted to a pH 11-12. The reaction was stirred for over 5-6 hrs. The solid was collected by filtration followed by drying at 45-55° C. to give an off white to tan solid (76 g).

Yield: 93.0%; HPLC Purity: 99.8%

Method-2

Tert-butyl 4-(6-{[7-cyclopentyl-6-(dimethylcarbamoyl)-7H-pyrrolo[2,3-d]pyrimidin-2-yl]amino}pyridin-3-yl)piperazine-1-carboxylate (100 g) was added to the solution of distilled water (200 ml) and conc. HCl (250 ml) and stirred at 20-30° C. The reaction mass was slowly added into pre-chilled aq. NaOH at 0-10° C. Isopropyl alcohol (200 ml) and dichloromethane (500 ml) was added to the reaction mixture. The organic layer was concentrated under vacuum and to the residue was added dichloromethane (100 ml) and heptane (500 ml). The mixture was stirred at 20-30° C. The solid was filtered and dried under vacuum at 60-70° C. and collected as off-white to pale yellow solid.

Yield: 91.1.0%; HPLC Purity: 99.89%

¹H NMR (400 MHz DMSO) δ ppm 9.34-9.31 (br, 1H), 8.77 (s, 1H), 8.18-8.15 (d, J=9.2, 1H), 8.03-8.02 (d, J=2.8, 1H), 7.46-7.43(dd, J=2.8, J=9.2, 1H), 6.59 (s, 1H), 4.77-4.69 (m, 1H), 3.05-3.01 (m, 10 H), 2.84 (m, 4H), 2.43 (m, 2H), 2.19 (m, 1H), 1.97 (m, 4H), 1.64-1.63 (m, 2H)

Example 6

Preparation of Form-M (FIG. 1) of Ribociclib Succinate

Method-1

Ribociclib (2 g) in methanol (100 mL) was heated to 60-65° C. The reaction mixture was stirred for 5-10 min followed by addition of succinic acid (570 mg) at the same temperature. Reaction mixture was then cooled to ambient temperature and stirred for 2-4 hrs. The solid so formed was collected by filtration and dried to give Ribociclib succinate Form-M (2 g).

Yield: 79.0%; HPLC Purity=99.82%

¹H NMR (400 MHz DMSO) δ ppm 9.33 (s, 1H), 8.75 (s, 1H), 8.13-8.15 (d, J=8.8, 1H), 7.99-8.00 (d, J=2.8, 1H), 7.41-7.44 (dd, J=8.8, J=2.8, 2H), 6.58 (s, 1H), 4.69-4.73 (m, 1H), 3.14-2.99 (m, 14H), 2.41 (m, 2H), 2.31 (s, 4H), 1.95 (m, 4H), 1.61-1.62 (m, 2H).

Method-2

Ribociclib (2 g) in methanol (80 mL) was heated to a temperature of 60-65° C. The reaction mixture was stirred for 5-10 min followed by addition of methanolic solution of succinic acid (600 mg in 20 mL of methanol) at the same temperature. Reaction mixture was stirred for 1 hour at 60-65° C. then added acetone (100 mL).

The solid formed was collected by filtration and dried to give Ribociclib succinate form-M (2 g).

Yield: 79.0%; HPLC Purity: 99.88%

1H NMR (400 MHz DMSO) δ ppm 9.33 (s, 1H), 8.75 (s, 1H), 8.13-8.15 (d, J=8.8, 1H), 7.99-8.00 (d, J=2.8, 1H), 7.41-7.44 (dd, J=8.8, J=2.8, 2H), 6.58 (s, 1H), 4.69-4.73 (m, 1H), 3.14-2.99 (m, 14H), 2.41 (m, 2H), 2.31 (s, 4H), 1.95 (m, 4H), 1.61-1.62 (m, 2H).

Example-7

Preparation of Form-N (FIG. 2) of Ribociclib Succinate

Method-1

Ribociclib (2 g) and succinic acid (600 mg) were added in the solution of dichloromethane (30 mL) and methanol (10 mL) at 20-30° C. Reaction mixture was stirred for 50-60 min followed by addition of diisopropyl ether (20 mL) at the same temperature. The reaction mixture was stirred for 4-5 hrs. The solid so formed, was collected by filtration and dried to give Ribociclib succinate form-N (2.3 g).

Yield: 90%; HPLC Purity: 99.76%

Method-2

Ribociclib (2 g) and succinic acid (600 mg) were added in the solution of dichloromethane (30 mL) and methanol (10 mL) at 20-30° C. Reaction mixture was stirred for 50-60 min followed by addition of ethyl acetate (20 mL) at the same temperature. This reaction mixture was stirred for 4-5 hrs. The solid so formed, was collected by filtration and dried to give Ribociclib succinate form-N (2.3 g).

Yield: 90%; HPLC Purity: 99.72%

We claim:

1. A process for the preparation of a compound of formula V or a salt thereof,

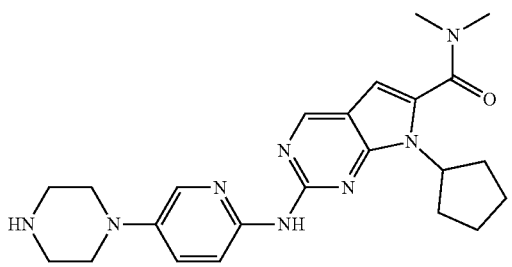

Formula V comprising the steps of:

a) reacting a compound of formula B,

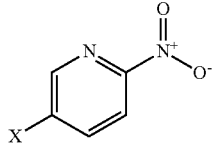

Formula B wherein X selected from bromo and chloro; with a compound of formula C,

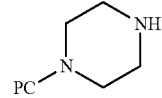

Formula C wherein PG is an amine protecting group;

in water in the presence of a base, which is sodium carbonate, potassium carbonate, diethylamine, N,N-diisopropylethylamine, or a combination thereof, to obtain a compound of formula A,

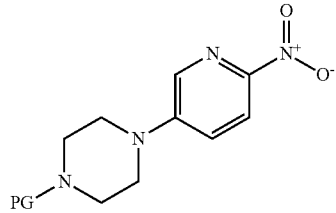

Formula A wherein PG is an amine protecting group;

b) converting the compound of formula A to the compound of formula V, and c) optionally, converting the compound of formula V to a salt.

2. The process according to claim 1, wherein the step b) comprises the steps of:

d) reacting the compound of formula A with zinc and acetic acid to obtain a compound of formula I,

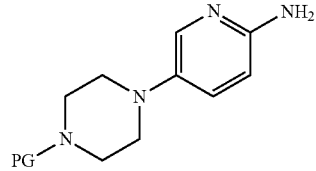

Formula I wherein PG is an amine protecting group;

e) reacting the compound of formula I with a compound of formula II,

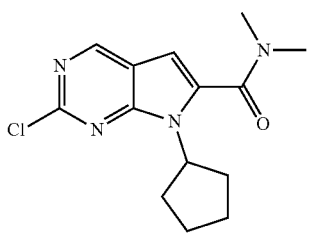

Formula II in the presence of a base to obtain a compound of formula III,

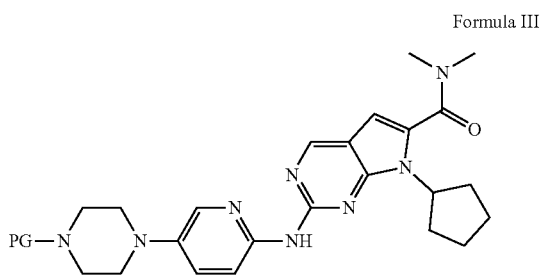

Formula III wherein PG is an amine protecting group;

f) de-protecting the compound of formula III to obtain an acid addition salt of formula IV,

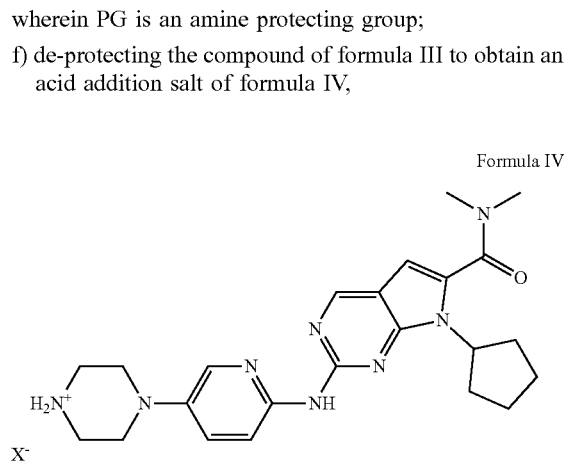

Formula IV wherein X⁻ is ion of the acid g) converting the compound of formula IV to a compound of formula V.

3. The process according to claim 2, wherein the step e) is carried out in presence of a metal halide catalyst.

4. The process according to claim 3, wherein the metal halide is copper (I) bromide, copper (I) iodide or copper (I) chloride.

5. The process according to claim 3, wherein the base to obtain a compound of formula III is sodium hydride or potassium tertiary butoxide.

6. The process according to claim 2, wherein the compound of formula III is a compound of formula IIIa,

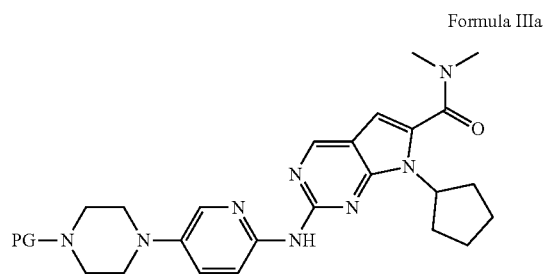

Formula IIIa wherein PG is tert-butoxycarbonyl (Boc).

7. The process according to claim 6, wherein the compound of formula IIIa is isolated as solid by adding water, methanol, or a mixture thereof.

8. The process according to claim 6, wherein the purity of the isolated compound of formula IIIa is greater than 99.6%, as measured by high-performance liquid chromatography (HPLC).

9. The process according to claim 2, wherein the de-protection is carried out in the presence of trifluoroacetic acid.

10. The process according to claim 2, wherein the acid addition salt of the compound of formula IV is a compound of formula IVa,

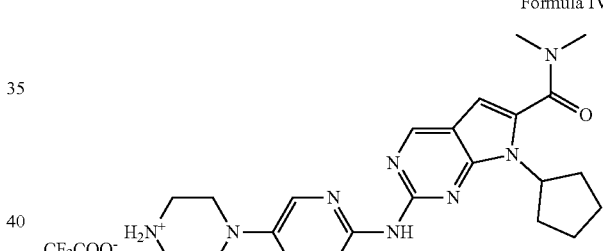

Formula IVa

11. The process according to claim 2, wherein the conversion of the compound of formula V to the salt is carried out by reacting the compound of formula V with succinic acid to obtain the compound of formula VI,

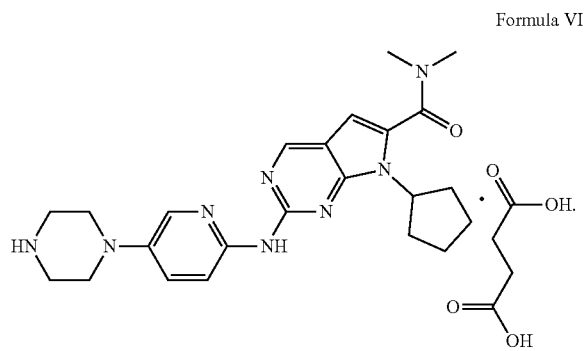

Formula VI

* * * * *